United States Patent
Goetz et al.

(10) Patent No.: US 9,471,752 B2
(45) Date of Patent: Oct. 18, 2016

(54) OPERATING ENVIRONMENT MONITOR FOR MEDICAL DEVICE PROGRAMMING

(75) Inventors: Steven M. Goetz, Brooklyn Center, MN (US); Touby A. Drew, Golden Valley, MN (US); Andrew H. Houchins, Lino Lakes, MN (US)

(73) Assignee: Medtronic, Inc., Minneapolis, MN (US)

(*) Notice: Subject to any disclaimer, the term of this patent is extended or adjusted under 35 U.S.C. 154(b) by 1911 days.

(21) Appl. No.: 11/949,347

(22) Filed: Dec. 3, 2007

(65) Prior Publication Data

US 2008/0141217 A1     Jun. 12, 2008

Related U.S. Application Data

(60) Provisional application No. 60/873,182, filed on Dec. 6, 2006.

(51) Int. Cl.
*G06F 19/00* (2011.01)
*G06F 9/445* (2006.01)
(Continued)

(52) U.S. Cl.
CPC ....... *G06F 19/3418* (2013.01); *G06F 9/44505* (2013.01); *G06F 9/4843* (2013.01);
(Continued)

(58) Field of Classification Search
CPC .. G06F 19/322; G06F 19/36; G06F 19/3412; G06F 19/3418; G06F 9/4881; G06F 21/6245; A61B 5/022; A61B 5/0002; A61B 2560/0271; A61B 1/37235; A61B 1/37282; A61N 1/37264
USPC ......... 717/100–101, 108–111, 114–116, 124, 717/126, 130–131, 165, 167, 171, 177; 706/924; 715/740–741, 748; 604/890.1–892.1, 100.2–100.03; 705/2–3; 702/85, 184–185; 707/609, 707/705, 758; 600/300; 607/30–32, 60, 63; 434/262, 267
See application file for complete search history.

(56) References Cited

U.S. PATENT DOCUMENTS 6,263,245 B1 *  7/2001  Snell ............................... 607/60
6,304,788 B1 * 10/2001  Eady et al. ...................... 700/86
(Continued)

FOREIGN PATENT DOCUMENTS

EP      1684172    *  7/2006
EP      1722310    * 11/2006
(Continued)

OTHER PUBLICATIONS

Richard C. Fries et al. "Medical Device Software Development",Clinical Engineering Handbook, 2004, pp. 359-365.*
(Continued)

*Primary Examiner* — Srirama Channavajjala
(74) *Attorney, Agent, or Firm* — Shumaker & Sieffert, P.A.

(57) ABSTRACT

A programming system for an electronic medical device (EMD) is described. The programming system, as described in this disclosure, comprises a host computer, such as a general purpose computer in an in-clinic computer network, executing a software platform that provides an operating environment with which a user can interact to program an EMD. The software platform invokes monitoring software that ensures that the host computer satisfies criteria for safe operation of the operating environment, e.g., ensures that the host computer meets the minimum operating conditions required for reliable operation of the operating environment. In particular, the monitoring software may monitor system faults that occur during operation, as well as ensure that criteria for safe operation are satisfied prior to initiating the operating environment.

20 Claims, 5 Drawing Sheets (51) Int. Cl.
*G06F 9/48* (2006.01)
*A61N 1/372* (2006.01)

(52) U.S. Cl.
CPC ....... *G06F19/3406* (2013.01); *G06F 19/3412* (2013.01); *A61B 2560/0271* (2013.01); *A61N 1/37235* (2013.01); *A61N 1/37282* (2013.01)

(56) References Cited

U.S. PATENT DOCUMENTS

| | | | |
|---|---|---|---|
| 6,665,565 B1 | 12/2003 | Stomberg et al. | |
| 6,790,198 B1 | 9/2004 | White et al. | |
| 6,957,102 B2* | 10/2005 | Silver et al. | 607/2 |
| 6,961,617 B1* | 11/2005 | Snell | A61N 1/37264 607/30 |
| 6,983,423 B2 | 1/2006 | Dvorak et al. | |
| 7,389,144 B1* | 6/2008 | Osorio et al. | 607/29 |
| 2001/0023360 A1* | 9/2001 | Nelson | A61B 5/0031 607/60 |
| 2002/0049684 A1* | 4/2002 | Nagamoto | A61B 5/0002 706/1 |
| 2002/0072358 A1 | 6/2002 | Schneider et al. | |
| 2002/0082665 A1* | 6/2002 | Haller et al. | 607/60 |
| 2002/0091547 A1* | 7/2002 | Ohe | G06F 8/65 705/2 |
| 2002/0165437 A1* | 11/2002 | Chen | 600/300 |
| 2003/0018403 A1* | 1/2003 | Braun | G05G 9/047 700/45 |
| 2003/0037172 A1 | 2/2003 | Lacombe et al. | |
| 2003/0046677 A1* | 3/2003 | Lindberg et al. | 717/173 |
| 2003/0095648 A1* | 5/2003 | Kaib et al. | 379/106.02 |
| 2003/0149526 A1* | 8/2003 | Zhou et al. | 701/213 |
| 2003/0220819 A1* | 11/2003 | Burstein et al. | 705/3 |
| 2004/0122488 A1* | 6/2004 | Mazar | A61N 1/37252 607/60 |
| 2004/0127774 A1* | 7/2004 | Moore et al. | 600/300 |
| 2004/0193884 A1 | 9/2004 | Molaro et al. | |
| 2005/0251227 A1* | 11/2005 | Khoo | A61N 1/37211 607/60 |
| 2005/0267780 A1* | 12/2005 | Ray | G06F 19/3406 705/2 |
| 2005/0288737 A1* | 12/2005 | Feliss | A61B 5/0024 607/60 |
| 2006/0080654 A1* | 4/2006 | Shelton | 717/173 |
| 2006/0247710 A1 | 11/2006 | Goetz et al. | |
| 2007/0027506 A1* | 2/2007 | Stender | G06F 19/3412 607/60 |
| 2008/0184219 A1* | 7/2008 | Matsumoto | G06F 11/1433 717/170 |

FOREIGN PATENT DOCUMENTS

| | | | |
|---|---|---|---|
| WO | WO 93/08872 | * | 5/1993 |
| WO | WO 01/48676 | * | 7/2001 |
| WO | 2006/023636 A1 | | 3/2006 |
| WO | WO 2006/044406 | * | 4/2006 |

OTHER PUBLICATIONS

Guidance for Industry, FDA Reviewers and Compliance on Off-The-Shelf Software Use in Medical DevicesU.S. Department of Health and Human Services Food and Drug Administration Center for Devices and Radiological Health Office of Device Evaluation,Document issued on: Sep. 9, 1999, 29 pages.*
Reply to Written Opinion for corresponding patent application No. PCT/US2007/024760, filed Oct. 1, 2008, 14 pages.
Notification of Transmittal of the International Preliminary Report on Patentability for corresponding patent application No. PCT/US2007/024760, mailed Mar. 30, 2009, 11 pages.
Notification of Transmittal of the International Search Report and the Written Opinion of the International Searching Authority, or the Declaration, for corresponding patent application No. PCT/US2007/024760, mailed May 27, 2008, 11 pages.

* cited by examiner

OPERATING ENVIRONMENT MONITOR FOR MEDICAL DEVICE PROGRAMMING

This application claims the benefit of U.S. Provisional Application No. 60/873,182, filed Dec. 6, 2006, the entire content of which is incorporated herein by reference.

TECHNICAL FIELD

The invention relates to electronic medical devices (EMDs) and, more particularly, programmers for EMDs.

BACKGROUND

Electronic medical devices (EMDs), which may be implantable or external, typically have a dedicated patient therapy manager (PTM) that patients use to interact with the medical device. PTMs, which may also be referred to as patient programmers, use software executed by an embedded microprocessor to perform communication tasks. PTMs are more secure than off-the-shelf computing devices, because PTMs are dedicated and customized to the task of interfacing with the EMD. PTMs generally run custom operating systems and are limited in their input/output capabilities.

EMDs also typically are configured to interact with a dedicated clinician programmer that may be used to perform advanced device setup and diagnostic capabilities. A clinician programmer may communicate directly with the EMD. Some clinician programmers may additionally communicate with a PTM. Like PTMs, clinician programmers are generally dedicated and customized to the task of interfacing with the EMD. Additionally, clinician programmers generally run custom operating systems and are limited in their input/output capabilities.

SUMMARY

In general, the invention relates to a programmer for an electronic medical device (EMD). A programmer, as described in this disclosure, comprises a host computer, such as a general purpose computer in an in-clinic computer network, executing a software platform that provides an operating environment with which a user can interact to program an EMD. The software platform invokes monitoring software that ensures the host computer satisfies criteria for safe operation of the operating environment, i.e., ensures that the host computer meets the minimum operating conditions required for reliable operation of the operating environment. The monitoring software may also monitor system faults that may occur during operation.

A user may operate the host computer for general purpose applications and as a programming device for an EMD in place of a dedicated programming device, such as a clinician programmer or a patient programmer. Dedicated programming devices generally run on custom operating systems that are designed to be more secure than off-the-shelf computing devices. However, the software platform executing on the host computer invokes monitoring software, which may ensure that the host computer satisfies criteria for safe operation as a programmer for the EMD. The monitoring software may also insulate the host computer from external hazards, e.g., system faults, which may cause the host computer to operate improperly as a programmer for the EMD. In other words, the software platform and, more particularly, the monitoring software enable a general purpose computer to also be reliably operated as a programming device for an EMD.

For example, the monitoring software may monitor various operating conditions of the host computer, such as processing bandwidth, data storage capacity, compatibility with software currently executing, communication quality and security, status of required applications, status of required system components, user authorization, and other conditions that may affect the operation of the operating environment. The monitoring software may also monitor system faults, e.g., a physical system fault such as a hard disk failure, to ensure safe operation of the operating environment provided by the software platform. In this manner, the software platform may enable the host computer to operate as a programming device for an EMD with at least the same level of security and performance provided by a dedicated programming device.

In one embodiment, the invention is directed to computer system comprising a host computer that is communicatively coupled to an electronic medical device (EMD), and a software platform executing on the host computer that invokes programming software and monitoring software. A user interacts with the programming software to program the EMD. The monitoring software ensures that the host computer satisfies criteria for safe operation of the programming software.

In an additional embodiment, the invention is directed to a method comprising launching a software platform that executes on a host computer, wherein the host computer is communicatively coupled to an electronic medical device (EMD), invoking programming software that runs on the software platform, wherein a user interacts with the programming software to program operation of the EMD, and invoking monitoring software that runs on the software platform. The monitoring software ensures that the host computer satisfies criteria for safe operation of the programming software.

In an additional embodiment, the invention is directed to a computer-readable medium comprising instructions. The instructions causing a programmable processor to launch a software platform that executes on a host computer that is communicatively coupled to an electronic medical device (EMD), invoke programming software that runs on the software platform, wherein a user interacts with the programming software to program operation of the EMD, and invoke monitoring software that runs on the software platform, wherein the monitoring software ensures that the host computer satisfies criteria for safe operation of the programming software.

The disclosure may provide one or more advantages. The software platform may execute on a general purpose computer, e.g., as a layer of functionality on top of an off-the-shelf operating system. As a result, the general purpose computer may be used for programming an EMD and other applications, such as access an electronic medical record (EMR) system. In addition, using a general purpose computer to program the EMD may be more cost efficient than using a dedicated device that is customized to the task of interfacing with the EMD and is otherwise limited in functionality, such as a clinician programmer or patient programmer.

The details of one or more embodiments of the invention are set forth in the accompanying drawings and the description below. Other features, objects, and advantages of the invention will be apparent from the description and drawings.

DETAILED DESCRIPTION

Figure 1:
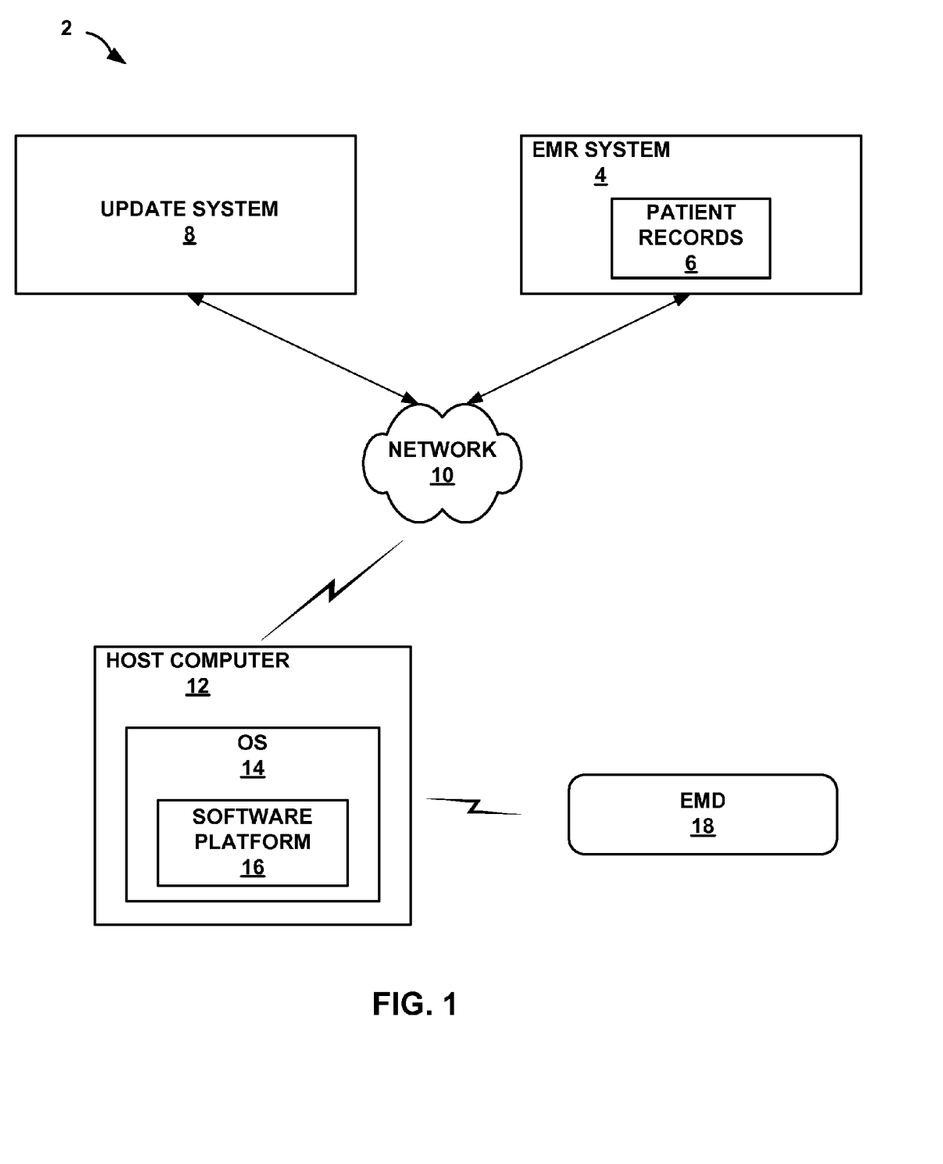
FIG. 1 is a block diagram illustrating an example computer network in which a host computer is used as a programming device for an electronic medical device (EMD).

FIG. 1 is a block diagram illustrating an example computer network 2 in which a host computer 12 is used to program an electronic medical device (EMD) 18. Host computer 12 may be a general purpose computer running an off-the-shelf operating system, and interfaces with EMD 18 to allow one or more users to program EMD 18. In this manner, a user may operate host computer 12 as a programming device for EMD 18, and to perform various functions or tasks required for other applications, i.e., applications not related to programming EMD 18.

EMD 18 may be any of a variety of medical devices that may communicate with host computer 12. For example, EMD 18 may take the form of an implantable medical device (IMD), such as an implantable defibrillator, an implantable pacemaker/cardioverter/defibrillator, an implantable muscular stimulus device, an implantable brain stimulator, an implantable neurostimulator, an implantable drug delivery device, an implantable physiological parameter monitor, or the like. However, EMD 18 is not necessarily an implantable device. In some embodiments, EMD 18 may be a medical device that is not implanted within a patient. In short, EMD 18 may be any of a variety of medical devices, including implantable and external medical devices, used to deliver therapy or perform diagnosis in humans, mammals, or other types of living beings.

An EMD, such as EMD 18, typically interfaces with a dedicated programming device or programmer, such as a clinician programmer or a patient programmer. A clinician programmer may be a computing device that permits a clinician to program therapy for a patient, e.g., using input keys and a display. For example, a clinician may operate a clinician programmer to perform advanced device setup and diagnostic capabilities. In this way, a clinician may operate a clinician programmer to specify parameters for use in delivery of therapy, such as electrical stimulation, drug administration, or the like. In addition, the clinician programmer may receive diagnostic information, sensed conditions associated with the patient, information relating to therapy delivered to the patient, or any other information collected or identified by the EMD.

The functionality of a patient programmer, however, is typically more restricted. A patient programmer may be a handheld computing device including a display and input keys that allow a patient to interact with the programmer and the EMD. For example, a patient may use a patient programmer to start, stop, or adjust therapy. In embodiments in which the EMD is an electrical stimulator, for example, the patient may use the patient programmer to adjust stimulation parameters such as duration, amplitude, pulse width, and pulse rate within an adjustment range specified via a clinician programmer, or select from a library of stored stimulation therapy programs using the patient programmer. In embodiments in which the EMD is a drug delivery pump, as another example, the patient may use the patient programmer to request delivery of a bolus, change an infusion rate, or the like.

In any case, clinician and patient programmers are generally dedicated computing devices customized to the task of interfacing with the EMD. That is, clinician and patient programmers use customized operating systems and software coupled to an embedded microprocessor for programming and performing communication tasks. As a result, the clinician and patient programmers are more secure than off-the-shelf computing devices, but are limited in their input/output capabilities.

In the illustrated example, however, host computer 12 may be a general purpose computer that can be operated to program EMD 18 and perform various functions or tasks required for other applications, i.e., applications not related to programming EMD 18. That is, host computer 12 is not a dedicated computing device that runs a custom operating system for performing a specific task. Rather, host computer 12 may perform functions or tasks required for various types of applications in addition to providing an interface for programming therapy delivered by EMD 18. Host computer 12 may provide an interface similar to a patient or clinician programmer interface for programming EMD 18. Consequently, host computer 12 may be used in place of a dedicated programming device to program EMD 18.

Host computer 12 may communicate with EMD 18 via cables or a wireless communication link. As an example, host computer 12 may communicate via wireless communication using near- or far-field radio frequency (RF) telemetry techniques known in the art. In another example, host computer 12 may communicate with EMD 18 using any of a variety of local wireless communication techniques, such as RF communication according to the Institute of Electrical and Electronic Engineers (IEEE) 802.11 or Bluetooth specification sets, infrared communication, e.g., according to the Infrared Data Association (IrDA) standard, or other standard or proprietary telemetry protocols. Further, host computer 12 may communicate with EMD 18 via remote telemetry techniques known in the art, such as communicating via a local area network (LAN), wide area network (WAN), public switched telephone network (PSTN), or cellular telephone network. However, host computer 12 and EMD 18 need not communicate wirelessly. In other embodiments, host computer 12 and EMD 18 may communicate via a wired communication, such as via a serial communication cable, or via exchange or removable media, such as magnetic or optical disks, or memory cards or sticks.

As described in detail in this disclosure, host computer 12 may comprise a personal computer, laptop, handheld computer, workstation, or other general purpose computing device running an off-the-shelf operating system 14. General purpose computers running off-the-shelf operating systems may be configured to perform functions related to various different applications, e.g., word processing applications, spread sheet applications, web browsing applications, data processing applications, graphics applications, email applications, multimedia playback applications, video gaming applications, and other general purpose applications. Examples off-the-shelf operating systems include a Microsoft Windows operating system, a Mac OS X operating system, a UNIX operating system, a Linux operating system, a Solaris operating system, or the like. Host computer 12 is not limited to a single computing device, and may in some embodiments comprise any number of connected devices. Furthermore, host computer 12 may comprise a computing device coupled to other devices, such as printers, monitors, pointing devices, or other peripheral devices.

In the example illustrated in FIG. 1, host computer 12 may be a general purpose computer used to access an electronic medical records (EMR) system 4. In this case, host computer 12 may be located in a clinic and used for convenient access to patient records 6 during procedures such as implantation of EMD 18 within a patient (not shown), and additionally provide functionality similar to a traditional clinician programmer. However, host computer 12 is not necessarily limited to accessing patient records 6. Rather, host computer 12 may be used for various applications in a clinical environment. Moreover, host computer 12 is not limited to clinical settings. For example, host computer 12 may be configured to operate as a recreational personal computer in the home of a patient. In such examples, host computer 12 may be operated by the patient in whom EMD 18 is implanted, and provide similar functionality to a traditional, dedicated patient programmer.

As described in this disclosure, host computer 12 may also be used, with special-purpose programming software, as a programming device for EMD 18. In particular, host computer 12 executes a software platform 16 that provides an operating environment with which a user can interact to program EMD 18. Software platform 16 invokes monitoring software that ensures host computer 12 satisfies criteria for safe operation of the operating environment, i.e., ensures that host computer 12 meets the minimum operating conditions required for reliable operation of the operating environment. The criteria may include one or more operating conditions such as adequate processing bandwidth, adequate available memory and data storage capacity, software and operating system compatibility, system device (peripheral) availability, acceptable communications quality and security, and required applications/utilities running. The monitoring software also insulates the host computer from external hazards, e.g., system faults, which may cause host computer 12 to operate improperly as a programmer for the EMD.

In particular, software platform 16 may invoke the monitoring software to ensure that host computer 12 satisfies the criteria prior to allowing a user to operate host computer 12 as a programmer for EMD 18. In other words, when host computer 12 receives input from a user that causes software platform 16 to execute, software platform 16 invokes the monitoring software before invoking other software necessary for the operation of host computer 12 as a programmer for EMD 18. In this way, the monitoring software can determine if host computer 12 satisfies the criteria, i.e., meets the minimum operating conditions, for the other software to reliably operate. If host computer 12 satisfies the minimum operating conditions, software platform 16 invokes the other software and the user may operate host computer 12 as a programmer for EMD 18. However, if host computer 12 does not satisfy the minimum operating conditions, software platform 16 does not invoke the other software. In this case, software platform 16 may attempt to automatically resolve the operating conditions that are not satisfied, or solicit input from the user to resolve the unsatisfied operating conditions.

When the minimum operating conditions are satisfied, software platform 16 invokes other software modules to provide an operating environment with which a user can interact to program EMD 18. Monitoring software, in this case, substantially continuously monitors host computer 12 to ensure that host computer 12 meets the minimum operating conditions. Monitoring software also substantially continuously monitors host computer 12 for any system faults that may cause host computer 12 to operate improperly.

If an inadequate operating condition is detected, the monitoring software may automatically resolve the condition (when possible), alert the user of the condition, or solicit user actions to correct the condition. For example, if a software update is required to satisfy the minimum operating requirements, host computer 12 may automatically connect to update system 8 via network 10 to retrieve the required update. However, when an inadequate environment condition cannot be resolved by the monitoring software, software platform 16 may continue to operate with limited or substandard functionality, depending on the affected environment condition. Certain conditions may allow for a user override or exceptions for emergency operation. That is, certain conditions may allow for software platform 16 to operate while all of the criteria are not satisfied.

Update system 8 may be a local software server or a remote server from which updates for operating system 14 or software running on operating system 14 can be retrieved. Network 10 may be any private or public network, and may include one or more Local Area Networks (LANs), Wide Area Networks (WANs), Wireless LANs, or the like. Network 10 may also include one or more connected network devices (not shown), such as personal computers, laptop computers, handheld computers, workstations, servers, routers, switches, printers, fax machines or other devices. Host computer 12 may be coupled to network 10 wirelessly, e.g., via a wireless access point, as illustrated by the example of FIG. 1, or may be coupled via a wired connection, e.g., via an Ethernet connection.

In this manner, host computer 12 may be configured as a general purpose computer that may also reliably operate as a programmer for EMD 18. Host computers 12 may, therefore, replace more costly dedicated programming devices, such as clinician and patient programmers, that are customized to the task of interfacing with EMD 18 and are otherwise limited in functionality.

Figure 2:
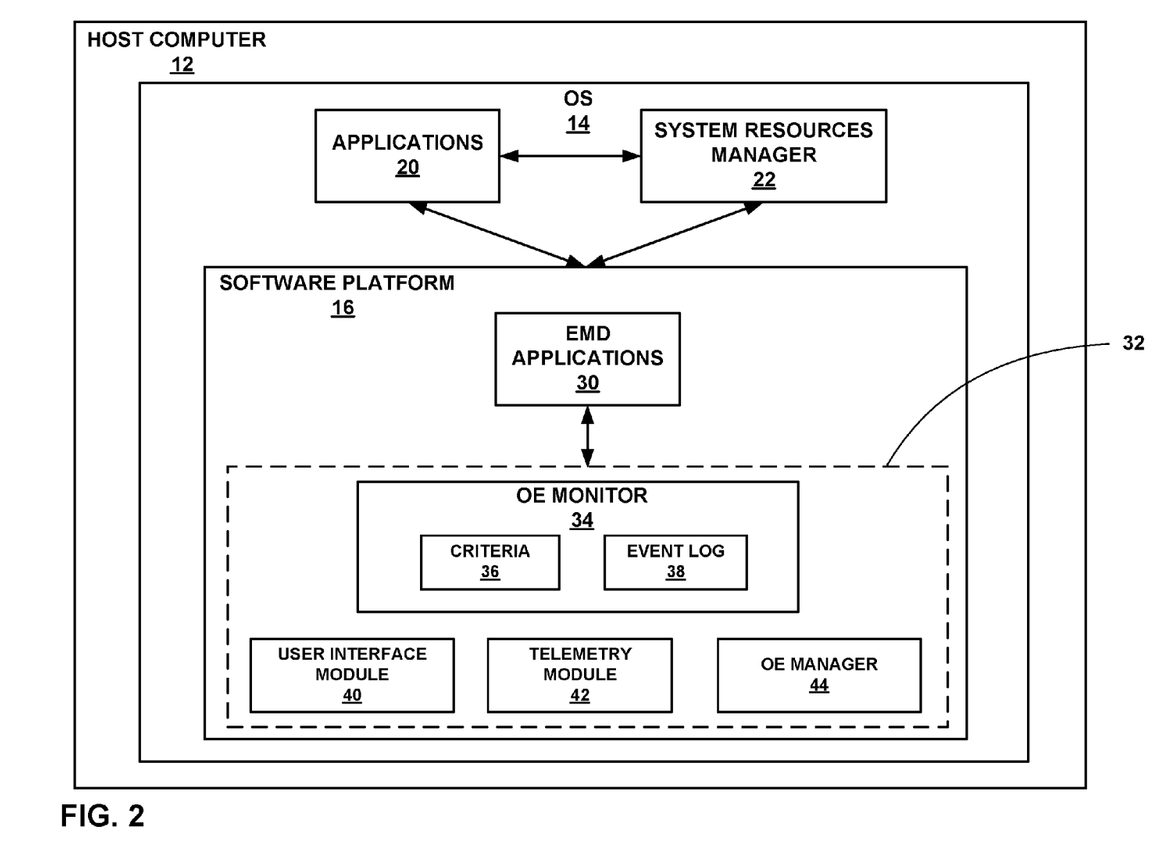
FIG. 2 is a block diagram illustrating the host computer in greater detail.

FIG. 2 is a block diagram illustrating host computer 12 in further detail. In the illustrated example of FIG. 2, host computer 12 includes operating system 14, and software platform 16 that runs on the operating system. Operating system 14 may comprise a Microsoft Windows operating system, a Mac OS X operating system, a UNIX operating system, a Linux operating system, a Solaris operating system, or other equivalent operating system configured to perform functions related to various applications, such as word processing applications, spread sheet applications, web browsing applications, data processing applications, graphics applications, email applications, multimedia playback applications, video gaming applications, and other general purpose applications. In general, operating system 14 manages hardware and software resources so that host computer 12 behaves in a flexible but predictable manner and provides a consistent application interface that allows applications to run on various computers regardless of their hardware configuration.

In FIG. 2, operating system 14 includes system resources manager 22 and applications 20. Applications 20 represent the various applications that may run on host computer 12. At any given time, one or more of applications 20 may be running. That is, more than one of applications 20 may be running on host computer 12 simultaneously. Applications 20 may, for example, include various different types of applications, such as word processing applications, spread sheet applications, web browsing applications, data processing applications, graphics applications, email applications, multimedia playback applications, video gaming applications, and other general purpose applications. In some embodiments, applications 20 may include an application that enables an authorized user to access EMR 4 to view and/or modify patient records 6 or other medical applications or records.

System resources manager 22 manages hardware and software resources to balance the needs of various processes associated with applications 20 with the availability of processing bandwidth, memory, data storage capacity, and input/output (I/O) bandwidth. In other words, system resources manager 22 balances the requirements of various processes associated with applications 20 with the availability of system resources.

Software platform 16, in general, provides an operating environment with which a user can interact to program EMD 18 (FIG. 1). For example, software platform 16 may comprise a layer of functionality implemented on top of operating system 14 that provides common functions and/or infrastructure for programming applications associated with EMD 18. Software platform 16, as shown in FIG. 2, includes EMD applications 30 for programming EMD 18, and possibly other EMDs, as well as software modules 32.

Software modules 32 implement the common platform functions for EMD applications 30. The functions may include drivers for connecting to a telemetry unit, a consistent interface for selecting a therapy and launching its application, standard tools for storing, manipulating, viewing, and managing session data, an interface to help features for operating EMD 18, and other features required for EMD applications 30. Each of EMD applications 30 may be an application that uses one or more of the common platform functions provided by software modules 32 to implement user interfaces and logic specific to a therapy device, e.g., EMD 18, or family of therapy devices.

Software modules 32, as shown in FIG. 2, include operating environment (OE) monitor 34, user interface module 40, telemetry module 42, and OE manager 44. User interface module 40 may implement functions that provide a consistent user interface to EMD applications 30. As an example, user interface module 40 may provide an interface similar to that of a dedicated clinician programmer for selecting a therapy and specifying therapy parameters for use in delivery of the therapy. In another example, user interface module 40 may provide an interface similar to that of a dedicated patient programmer for adjusting therapy parameters specified via a clinician programmer, or selecting a therapy program from a library of stored therapy programs.

Telemetry module 42 may implement functions that enable communication between host computer 12 and EMD 18 via RF techniques known in the art, or other wireless or wired communication techniques known in the art, such as 802.11 or Bluetooth specification sets, infrared communication according to the IrDA standard, or other standard or proprietary telemetry protocols.

OE monitor 34 ensures that host computer 12 satisfies criteria 36 for safe operation of the operating environment provided by software platform 16. Criteria 36 may comprise a list of minimum operating conditions that are required for safe, i.e., reliable, operation of the operating environment provided by software platform 16. For example, criteria 36 may include one or more operating conditions such as adequate processing bandwidth, adequate available memory and data storage capacity, software and operating system compatibility, system device (peripheral) availability, acceptable communications quality and security, and required applications/utilities running. Accordingly, software platform 16 and, more particularly, OE monitor 34 may interface with applications 20, system resources manager 22, and EMD applications 30 to monitor or track operating environment conditions. OE monitor 34 may also monitor system faults that may occur during operation and cause the operating environment to operate improperly. Example system faults include application errors generated by applications 20 or EMD applications 30, a disk drive failure, and other unexpected errors that may affect operating conditions of software platform 16.

OE monitor 34 may store a record of environment conditions and system faults in event log 38. For example, event log 38 may comprise a running log of environment conditions monitored by OE monitor 34. Event log 38 may comprise time stamped entries for each monitoring instance, i.e., each instance that OE monitor 34 monitors a particular condition. In this case, an entry in event log 38 may confirm that a particular condition satisfies criteria 38 or does not satisfy criteria 36. Alternatively, event log 38 may only include entries that indicate the condition that does not satisfy criteria 36. In this manner, event log 38 may be interrogated to evaluate performance and/or efficacy of host computer 12 operating as a programmer for EMD 18.

In operation, OE monitor 34 may be the first or one of the first of software modules 32 invoked by software platform 16. For example, with respect to FIG. 2, software platform 16 may invoke OE monitor 34 prior to invoking user interface module 40, telemetry module 42, and OE manager 44. In this case, OE monitor 34 may monitor operating system 14 and, more particularly, applications 20 and system resources manager 22 to determine if criteria 36 are satisfied. In other words, OE monitor 34 monitors applications 20 and system resources manager 22 to detect inadequate environment conditions. If host computer 12 satisfies criteria 36, i.e., OE monitor 34 does not detect any inadequate environment conditions, software platform 16 may invoke user interface module 40, telemetry module 42, OE manager 44, and any other necessary modules required to run the operating environment for EMD applications 30.

OE monitor 34 may also monitor environment conditions during operation to insulate EMD 18 from external hazards, i.e., system faults, that may cause improper operation of EMD 18. OE monitor 34 may monitor operating conditions at pre-determined periodic intervals. Thus, OE monitor may monitor one or more operating conditions every approximately three seconds to approximately five seconds, every approximately one second to approximately three seconds, approximately every second, more than once per second, or substantially continuously.

In the event that OE monitor 34 detects an inadequate environment condition, OE monitor 34 may invoke OE manager 44. OE monitor 34 may, for example, notify OE manager 44 of the inadequate operating condition by transmitting a signal or message to OE manager 44. Upon receiving notification of the inadequate operating condition, OE manager 44 may automatically resolve the condition (when possible), alert the user of the condition, or solicit user actions to correct the inadequate condition. For example, OE manager 44 may automatically resolve an inadequate condition by retrieving an update from update system 8 (FIG. 1).

OE manager 44 may also automatically resolve an inadequate environment condition by communicating with systems resource manager 22 to coordinate management of system resources. In this case, OE manager 44 and system resources manager may communicate with each other to automatically terminate non-essential applications, automatically archive infrequently or least recently accessed data on network storage, automatically select alternate communications, or automatically enable appropriate security features.

In another example, OE manager 44 may generate a display window that notifies the user of the inadequate condition. In an additional example, OE manager 44 may also receive input from the user that indicates what action should be taken to resolve the condition. In this case, the display window that prompts the user may also receive input from the user.

Table 1 below summarizes example conditions that may be encountered and example solutions that may be implemented by OE manager 44. In Table 1, the left hand column specifies the condition detected by OE monitor 34, and the right hand column specifies a list of example actions that may be taken by OE manager 44 to resolve the corresponding condition in the left hand column. Host computer 12, however, is not limited to the example conditions and solutions provided in Table 1 below.

TABLE 1

Operating Environment Conditions and Possible Solutions

| Condition | Solutions |
| --- | --- |
| Inadequate processing bandwidth | Increase processing priority<br>Delay or omit non-essential processing<br>Request termination of non-essential processing (e.g., non-essential applications) |
| Inadequate memory or data storage capacity | Request termination of non-essential applications<br>Request user disposal of non-essential data<br>Request insertion of movable media (for data storage)<br>Automatically archive infrequently or least recently accessed data on network storage |
| Software incompatibility | Warn user of software incompatibility (e.g., OS, drivers, etc.)<br>Request user approval of software upgrade<br>Automatically upgrade software |
| Peripheral device unavailable | Seek alternate device |
| Unacceptable communication quality or security | Request repositioning or verification of communication connections<br>Automatically select alternate communications channel<br>Automatically select alternate communications method<br>Requesting user confirmation to proceed with inadequate security<br>Automatically enable security |
| Required components not running (e.g., virus software, firewall) | Automatically launch required applications |
| Inadequate user permissions | Proceed with limited functionality<br>Notify user and prevent execution |
| Unsatisfied hardware condition (e.g., unsatisfied MAC address verification) | Notify user and prevent execution |

In some cases, however, OE manager 44 may be unable to resolve one or more inadequate environment conditions automatically or after receiving input for a user. In this case, OE manager 44 may prevent software platform 16 from further execution and alert the user of the situation or, alternatively, cause software platform 16 to operate with limited functionality depending on the affected environment condition. In fact, certain conditions may allow for a user override or exceptions for emergency operation. For example, if there is inadequate data storage, software platform 16 may continue to operate without saving records of the programming session. As another example, if network access to patient records 6 is not available, software platform 16 may continue to operate without this information and treat the patient as a new or anonymous patient. As another example, OE monitor 34 or OE manager 44 may determine that a software upgrade is required to support a certain EMD, but OE manager 44 may allow software platform to continue to operate without the upgrade to interact with EMDs supported by the currently installed software.

Figure 3:
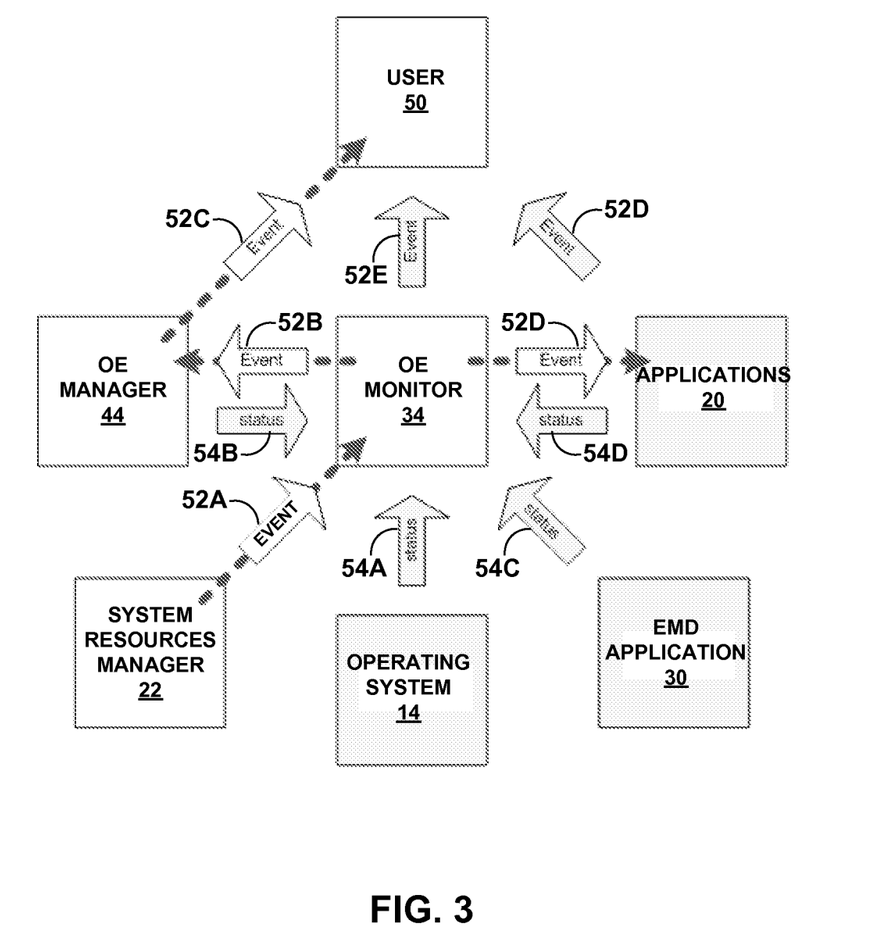
FIG. 3 is a block diagram that illustrates communication between an operating environment monitor and other system components of the host computer.

FIG. 3 is a block diagram that illustrates communication between OE monitor 34 and other system components of host computer 12. The system components illustrated in FIG. 3 include operating system 14, applications 20, system resources manager 22, EMD application 30, and OE manager 44. User 50 is also illustrated in FIG. 3 to show communication between OE monitor 34 and user 50 operating host computer 12.

In FIG. 3, arrows 54A-54D indicate "status messages" (collectively, "status messages 54") sent to OE monitor 34 by operating system 14, OE manager 44, EMD application 30, and applications 20, respectively. As previously described, these system components may send respective status messages periodically. OE monitor 34 monitors the status of these system components by inspecting these status messages 54 and comparing information included in the status messages to criteria 36. In this manner, OE monitor 34 can detect an inadequate operating condition and send notification of the inadequate condition or "event" to affected system components. In FIG. 3, arrows 52A-52D represent an event message or other form of notification (collectively, "event messages 52") that is transmitted between system components. Event messages 52A-52D may include information identifying the inadequate operating condition or system fault. In some cases, the event message may also include information specifying recommended actions for resolving the inadequate operating condition or system fault.

As shown in FIG. 3, an event message 52 may be transmitted from OE monitor 34 to one of the illustrated system components, or may be transmitted from one of the system components to OE monitor 34, user 50, or another system component. As an example, OE monitor 34 may transmit an event message 52 to a system component in response to receiving a status message 54 from another system component and detecting and inadequate environment condition based on the status message. A system component may also transmit an event message 52 in place of a status message in response to experiencing or detecting a system fault. In this case, the system component may immediately transmit the event message 52 to OE monitor 34 rather than waiting until a pre-determined time for transmitting a status message 54. OE monitor 34 may then transmit additional event messages 52 to other system components affected by the system fault.

In FIG. 3, arrow 52A indicates that system resources manager 22 transmits an event message to OE monitor 34. System resource manager 22 may transmit the event message 52A in response to detecting a system fault in host computer 12. The system fault may be an inadequate environment condition or system fault detected by system resources manager, such as inadequate processing bandwidth, inadequate memory or storage capacity, peripheral device unavailability, unacceptable communication quality or security, or other system fault, such as a hard disk failure or other physical system fault.

OE monitor 34 receives the event message from system resources manager 22 as well as status messages from the other illustrated system components as indicated by arrows 54A-54D. OE monitor 34 may receive the event message and status messages at substantially the same time or at different times. In any case, OE monitor 34 may process the received event message to identify the system fault. Based on the event message OE monitor 34 may determine which system components to alert to the identified system fault. In the example of FIG. 3, OE monitor 34 transmits event messages, indicated by event arrows 52B and 52D, to OE manager 44 and applications 20, respectively.

OE manager 44 may interrogate the received event message to identify the system fault. Based on the system fault, OE manager 44 may determine which, if any, actions to take to resolve the identified system fault or inadequate environment condition. In some embodiments, OE manager 44 may select one or more actions for resolving the system fault or inadequate environment condition in accordance with a set of rules or pre-programmed logic. Example inadequate operating conditions and responses to the inadequate operating conditions are provided in previously presented Table 1.

In response to receiving the event messages from OE monitor 34, OE manager 44 and applications 20 may transmit event messages indicated by event arrows 52C and 52D to user 50. The event messages indicated by event arrows 52C and 52D may alert user 50 to the system fault and any action taken by OE manager 44 and/or applications 20 in response to the system fault. In this manner, FIG. 3 illustrates the transmission of status and event messages between system components of host computer 12 in response to system resources manager 22 detecting a system fault or inadequate environment condition. In particular, OE monitor 34 may monitor the status of the system components by receiving status messages from each of the system components periodically. OE monitor 34 may also transmit event messages to alert the appropriate system components, and possibly user 50, to a detected event. In some embodiments, OE monitor 34 may transmit an event message to OE manager 44. Upon receiving the event message, OE manager 44 may attempt to automatically resolve the system fault or inadequate environment condition, for example, by communicating with system resources manager 22 to coordinate management of system resources.

Figure 4:
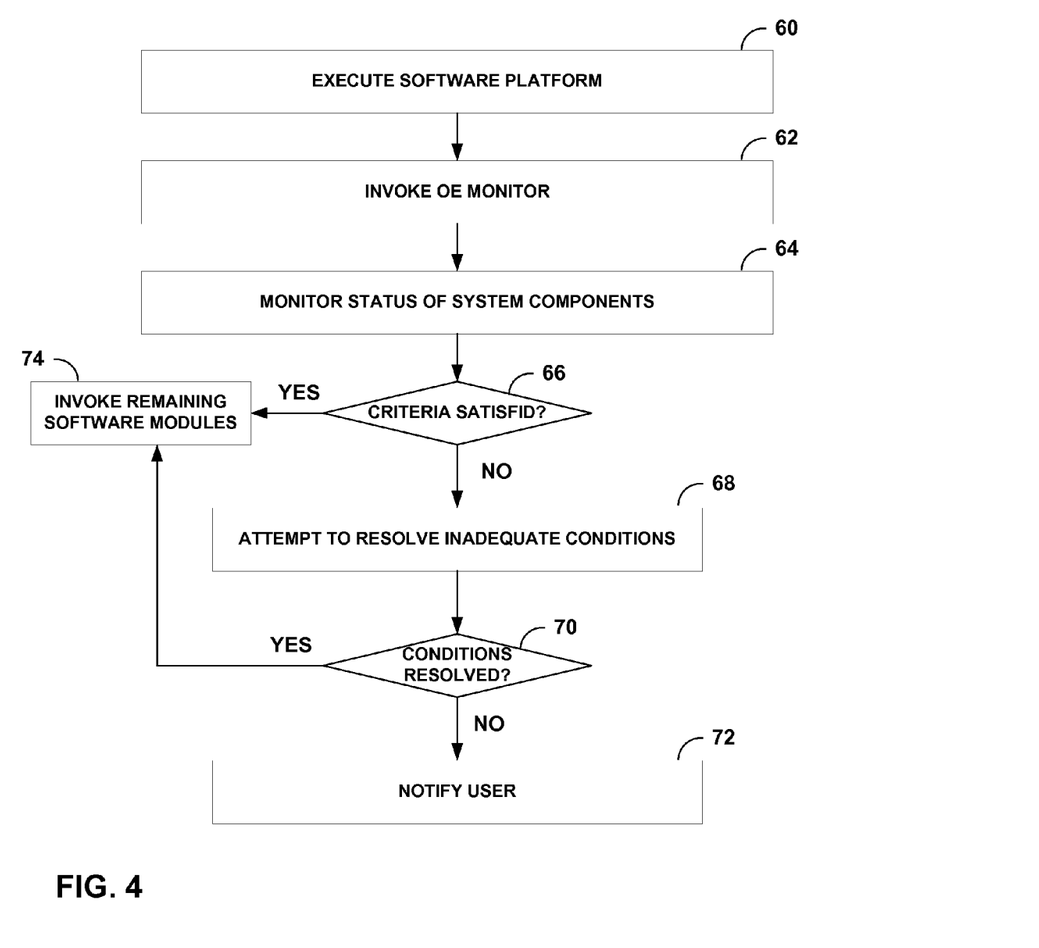
FIGS. 4 and 5 are flow diagrams illustrating example modes of operation of the host computer system for reliably operating the host computer as a programming device for the EMD.

FIG. 4 is a flowchart illustrating an example mode of operation of host computer 12. As previously described, host computer 12 may be a general purpose computer that runs an off-the-shelf operating system, which may also be used as a programmer for EMD 18. Thus, in some embodiments, host computer 12 may operate as a programmer only upon receiving a command or instructions from a user. FIG. 4 begins when host computer 12 receives a command from a user to execute software platform 16 (60). In general, software platform 16 provides an operating environment with which the user can interact to program EMD 18. More specifically, software platform 16 ensures that host computer 12 satisfies criteria 36 for safe operation of the operating environment, i.e., meets the minimum requirements required for reliable operation of the operating environment.

When software platform 16 begins to execute on host computer 12, software platform invokes OE monitor 34 (62). OE monitor 34 monitors the status of system components (64) to determine if host computer 12 satisfies criteria 36 (66). OE monitor 34 may monitor, for example, applications 20 and system resources manager 22 to detect any system faults or inadequate system conditions. As described with respect to FIG. 3, OE monitor 34 may interrogate status messages received from each system component to determine if the criteria are satisfied.

If the criteria are satisfied, software platform 16 may invoke the remaining software modules (74) required to operate host computer 12 as a programmer for EMD 18. For example, with respect to FIG. 2, software platform 16 may also invoke user interface module 40 and telemetry module 42.

However, in the event that criteria 36 are not satisfied, software platform 16 attempts to resolve the inadequate environment condition or system fault (68). In particular, a software module, such as OE manager 44, may attempt to resolve the inadequate environment condition by communicating with other system components, alerting the user and/or soliciting input from the user, or retrieving a system update from update system 8.

If the inadequate condition is resolved (70), software platform 16 may invoke the remaining software modules (74) required to operate host computer 12 as a programmer for EMD 18. If the inadequate condition is not resolved (70), OE monitor 34 may notify the user (72) of the condition that is preventing host computer 12 from being able to reliably execute software platform 16.

Figure 5:
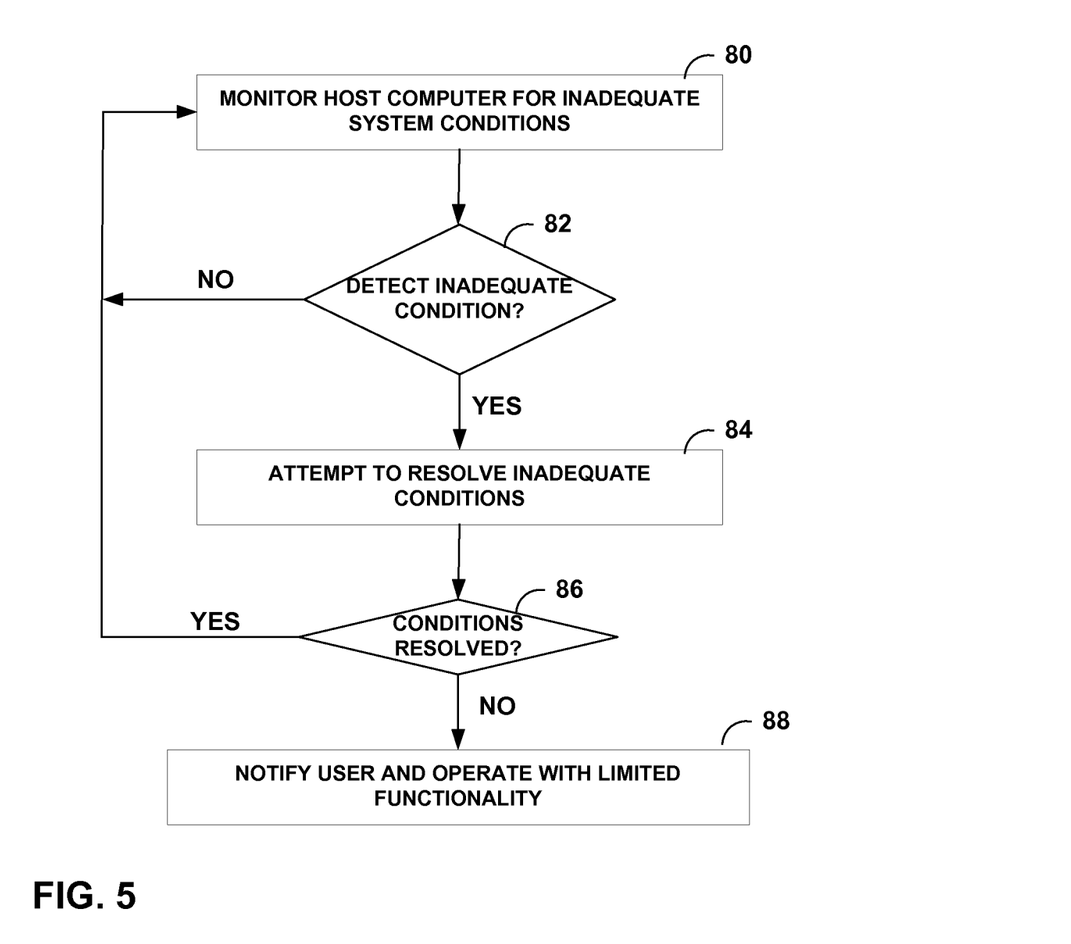

FIG. 5 is a flow chart illustrating another example mode of operation of host computer 12 for programming EMD 18. In FIG. 5, host computer 12 is operating as a programmer for EMD 18, i.e., software platform 16 is executing. In order to insulate host computer 12 from hazards that may cause host computer 12 to fail to operate properly, software platform 16 monitors host computer 12 for system faults and/or inadequate system requirements (80). For example, OE monitor 34 may monitor applications 20 and system resources manager 22 running on operating system 14, and EMD applications 30 and software modules 32 running on software platform 16 to detect inadequate environment conditions.

If no inadequate conditions are detected (82), OE monitor 34 continues to monitor the host computer for inadequate system conditions (80). On the other hand, if OE monitor 34 detects any inadequate environment conditions (82), software platform 16, e.g., OE manager 44, attempts to resolve the detected condition (84). If, after attempting to resolve the inadequate condition, the inadequate condition is not resolved (86), software platform 16 may notify the user and/or operate with limited or substandard functionality (88) depending on the inadequate environment condition. If the detected condition is resolved (86), OE monitor 34 returns to monitoring the host computer for inadequate system conditions (80).

If an inadequate environment condition cannot be resolved by the monitoring software, software platform 16 may continue to operate with limited or substandard functionality, depending on the affected environment condition. In this manner, software platform 16 may repeat steps 80, 82, 84, and 86 as necessary to continuously monitor operation of host computer 12.

Various embodiments of the invention have been described. However, the invention is not limited to the described embodiments. For example, the invention is not limited to embodiments in which an operating environment monitor is invoked just prior to modules associated with programming an EMD. In some embodiments, some or all of the functionality of an operating environment monitor as described herein may be a persistent or periodic background process that collects information regarding the status of the operating environment during non-EMD programming operation of the operating system. In such embodiments, the operating environment monitor may take any of the actions described above based on such information during non-EMD programming operation of the operating system, or when a user attempts to launch the EMD programming software platform.

Furthermore, the invention is not limited to embodiments in which the operating environment monitor executes on a general purpose computer. In some embodiments, the operating environment monitor may be provided on a dedicated programming device to facilitate its safe operation. In some examples, the memory, e.g., the RAM or ROM, of host computer 12 may function as a computer-readable storage medium. In these examples, because the memory is a hardware device, the computer-readable storage medium may be referred to as a non-transitory computer-readable storage medium to indicate that the storage medium is not a transitory signal or propagated media. The memory of host computer 12 may store instructions that cause a programmable processor of host computer 12 to launch software platform 16 on host computer 12. As described above, the launching of software platform 16 may cause host processor 12 to invoke programming software to program operation of EMD 18 and monitoring software to ensure that host computer 12 satisfies criteria for safe operation. These and other embodiments are within the scope of the following claims.

The invention claimed is:

1. A computer system comprising:
a host computer that is communicatively coupled to an electronic medical device (EMD);
an operating system executing on the host computer;
a software platform executing on the host computer that executes programming software that runs on the host computer via the software platform to allow a user to program the EMD with the host computer, and monitoring software that runs on the host computer via the software platform, wherein the software platform executes as a layer of functionality above the operating system; and
one or more general purpose applications executing on the operating system, wherein the general purpose applications and software platform execute at the same time,
wherein the software platform executes the monitoring software prior to executing the programming software,
wherein the monitoring software determines whether the host computer satisfies at least one of a processing bandwidth criteria or a general purpose application compatibility criteria for operation of the programming software,
wherein the software platform disables at least one of the general purpose applications in response to the monitoring software determining that the host computer does not satisfy the at least one of the processing bandwidth criteria or the general purpose application compatibility criteria, and
wherein the software platform executes the programming software in response to the monitoring software determining that the host computer satisfies the at least one of the processing bandwidth criteria or the general purpose application compatibility criteria.

2. The computer system of claim 1, wherein the host computer is a general purpose computer.

3. The computer system of claim 1, wherein the monitoring software at least one of prevents, suspends, or limits operation of the software platform when the at least one of the processing bandwidth criteria or the general purpose application compatibility criteria are not satisfied.

4. The computer system of claim 3, wherein, in response to detecting that the at least one of the processing bandwidth criteria or the general purpose application compatibility criteria are not satisfied and prior to at least one of preventing, suspending, or limiting operation of the software platform, the monitoring software attempts to automatically resolve a detected condition that causes the at least one of the processing bandwidth criteria or the general purpose application compatibility criteria to not be satisfied.

5. The computer system of claim 3, wherein, in response to detecting that the at least one of the processing bandwidth criteria or the general purpose application compatibility criteria are not satisfied and prior to at least one of preventing, suspending, or limiting operation of the software platform, the monitoring software prompts the user to resolve a detected condition that causes the criteria at least one of the processing bandwidth criteria or the general purpose application compatibility criteria to not be satisfied.

6. The computer system of claim 1, wherein the monitoring software monitors the host computer during execution of the software platform to ensure that the host computer satisfies the at least one of the processing bandwidth criteria or the general purpose application compatibility criteria during execution of the software platform.

7. The computer system of claim 1, wherein the host computer communicates with the EMD via wireless telemetry.

8. The computer system of claim 1, wherein the host computer accesses an electronic medical records (EMR) system under the control of the user.

9. The computer system of claim 1, wherein:
the monitoring software determines whether the host computer satisfies a criteria for minimum data storage capacity for operation of the programming software; and
the software platform archives data of the host computer on a storage device connected to the host computer by a network in response to determining that the host computer does not satisfy the criteria for minimum data storage capacity.

10. The computer system of claim 1, wherein:
the monitoring software determines whether the host computer satisfies a user permission criteria for operation of the programming software;
the programming software has a plurality of features;
in response to the monitoring software determining that the host computer does not satisfy the user permission criteria, the software platform disables at least a portion of the plurality of features of the programming software and executes the programming software; and
in response to the monitoring software determining that the host computer satisfies the user permission criteria, the software platform enables each feature of the plurality of features of the programming software and executes the programming software.

11. The computer system of claim 1, wherein:
the host computer is communicatively coupled to the EMD along a first communications channel;

the monitoring software determines whether the host computer satisfies a criteria for secure operation of the programming software along the first communications channel; and in response to determining that the host computer does not satisfy the criteria for secure operation of the programming software along the first communications channel, the software platform selects a second communications channel for communication between the host computer and the EMD.

12. A method comprising:

executing an operating system on a host computer;

launching a software platform that executes on the host computer, wherein the host computer is communicatively coupled to an electronic medical device (EMD);

executing programming software that runs on the host computer via the software platform to allow a user to program operation of the EMD with the host computer, wherein the software platform executes as a layer of functionality above the operating system;

executing one or more general purpose applications on the operating system, wherein the general purpose applications and software platform execute at the same time; and prior to executing the programming software, executing monitoring software that runs on the host computer via the software platform and determines whether the host computer satisfies at least one of a processing bandwidth criteria or a general purpose application compatibility criteria for operation of the programming software, wherein executing the programming software comprises:
determining, by the monitoring software, whether the host computer satisfies the at least one of the processing bandwidth criteria or the general purpose application compatibility criteria prior to executing the programming software; and
executing the programming software in response to the monitoring software determining that the host computer satisfies the at least one of the processing bandwidth criteria or the general purpose application compatibility criteria.

13. The method of claim 12, wherein the host computer is a general purpose computer.

14. The method of claim 12, further comprising, by the monitoring software, at least one of preventing, suspending, or limiting operation of the software platform when the criteria at least one of the processing bandwidth criteria or the general purpose application compatibility criteria are not satisfied.

15. The method of claim 14, further comprising, in response to detecting that the at least one of the processing bandwidth criteria or the general purpose application compatibility criteria are not satisfied and prior to at least one of preventing, suspending, or limiting operation of the software platform, attempting to automatically resolve a detected condition that causes the at least one of the processing bandwidth criteria or the general purpose application compatibility criteria to not be satisfied by the monitoring software.

16. The method of claim 14, further comprising, in response to detecting that the at least one of the processing bandwidth criteria or the general purpose application compatibility criteria are not satisfied and prior to at least one of preventing, suspending, or limiting operation of the software platform, prompting the user to resolve a detected condition that causes the at least one of the processing bandwidth criteria or the general purpose application compatibility criteria to not be satisfied by the monitoring software.

17. The method of claim 12, wherein invoking monitoring software comprises monitoring the host computer with the monitoring software during execution of the software platform to ensure that the host computer satisfies the at least one of the processing bandwidth criteria or the general purpose application compatibility criteria during execution of the software platform.

18. A non-transitory computer-readable storage medium comprising instructions, the instructions causing a programmable processor to:

execute an operating system on a host computer launch a software platform that executes on the programmable processor of the host computer that is communicatively coupled to an electronic medical device (EMD);

execute programming software that runs on the host computer via the software platform to allow a user to program operation of the EMD with the host computer, wherein the software platform executes as a layer of functionality above the operating system;

execute one or more general purpose applications on the operating system, wherein the general purpose applications and software platform execute at the same time; and prior to executing the programming software, execute monitoring software that runs on the host computer via the software platform and determines whether the host computer satisfies at least one of a processing bandwidth criteria or a general purpose application compatibility criteria for operation of the programming software, wherein the instructions that cause the programmable processor to execute the programming software comprise instructions that cause the programmable processor to:
determine, with the monitoring software, whether the host computer satisfies the at least one of the processing bandwidth criteria or the general purpose application compatibility criteria prior to executing the programming software; and
execute the programming software in response to the monitoring software determining that the host computer satisfies the at least one of the processing bandwidth criteria or the general purpose application compatibility criteria.

19. The non-transitory computer-readable storage medium of claim 18, wherein the host computer is a general purpose computer.

20. The non-transitory computer-readable storage medium of claim 18, further comprising instructions that cause the monitoring software to at least one of prevent, suspend, or limit operation of the software platform when the at least one of the processing bandwidth criteria or the general purpose application compatibility criteria are not satisfied.

* * * * *